United States Patent [19]

Göbel et al.

[11] Patent Number: 4,600,390

[45] Date of Patent: Jul. 15, 1986

[54] APPARATUS AND METHOD FOR APPLYING A SILICON OXIDE-CONTAINING ADHESION-PROMOTING LAYER ON METALLIC DENTAL PROSTHESES

[75] Inventors: Roland Göbel; Rudolf Musil; Hans-Jürgen Tiller, all of Jena; Steffen Oppawsky, Bad Homburg; Albert Schmidt, Bad Homburg; Rolf Janda, Bad Homburg, all of Fed. Rep. of Germany

[73] Assignee: Kulzer & Co. GmbH, Wehrheim, Fed. Rep. of Germany

[21] Appl. No.: 686,211

[22] Filed: Dec. 26, 1984

[30] Foreign Application Priority Data

Feb. 4, 1984 [DE] Fed. Rep. of Germany ....... 3403894

[51] Int. Cl.$^4$ .................... A01N 1/02; A61C 5/08; B05B 7/06; B05C 5/00
[52] U.S. Cl. ..................... 433/218; 106/35; 118/315; 118/320; 118/715; 118/724; 118/729; 427/2; 427/422; 427/424; 427/425; 427/427
[58] Field of Search ............... 118/315, 320, 715, 724, 118/726, 729; 427/422, 423, 424, 425, 427; 106/35; 433/218, 212, 222, 223

[56] References Cited

U.S. PATENT DOCUMENTS

| | | | |
|---|---|---|---|
| 3,873,339 | 3/1975 | Hudson | 427/163 X |
| 4,212,663 | 7/1980 | Aslami | 118/726 X |
| 4,364,731 | 12/1982 | Norling et al. | 433/218 |

OTHER PUBLICATIONS

Dental-Labor XXX, issued Dec. 1982, p. 1711–1716.

Primary Examiner—Michael R. Lusignan
Attorney, Agent, or Firm—Frishauf, Holtz, Goodman & Woodward

[57] ABSTRACT

To apply a silicon oxide adhesion-promoting layer to a metal prosthesis part or frame, for subsequent application of a dental plastic thereon, the prosthesis is subjected to flame hydrolysis derived from a flame hydrolysis burner (11) which has a silicon compound in vapor or gas form applied thereto in addition to a carbon-containing combustion gas, such as propane and air, the prosthesis part or frame being passed through the flame from the burner in the forward third thereof, the burner flame cone having, in operation, a length (L) of between 15 to 20 cm, a gas stream speed of about 1 m/sec., and wherein the length (L) of the cone exceeds the spacing distance (D) of the farthest part of the prosthesis from the mouth of the burner by only up to about 25%. For fine adjustment of the cone, a tinting substance can be added to the flame.

20 Claims, 3 Drawing Figures

APPARATUS AND METHOD FOR APPLYING A SILICON OXIDE-CONTAINING ADHESION-PROMOTING LAYER ON METALLIC DENTAL PROSTHESES

The present invention relates to a method to coat, metallic dental prostheses with a coating which includes silicon oxide to form an adhesion-promoting layer for application of plastic dental material to the metallic dental prosthesis part, and to an apparatus to efficiently and effectively carry out the method.

BACKGROUND

Adhesion of plastic material of the dental type to metallic dental prosthesis articles or components, which may form a main structural frame of the final dental prosthesis presents some problems. Recently, methods have been proposed in which, to improve the adhesion, a silicon oxide-containing adhesion-promoting layer is applied to the metallic dental prosthesis part.

One process is described in the publication "Dental-Labor XXX". According to this publication, a glow discharge device is used. The metallic prosthesis part is placed into an evacuated chamber in which, under a pressure of between about 0.133 to 0.4 mbar, a glow discharge plasma is generated. A silicon compound, such as triethyloxymethylsilane, is added to the glow discharge plasma.

Another method is described in U.S. Pat. No. 4,364,731. To coat a metallic dental prosthesis part with a silicon oxide adhesion-promoting layer, a magnetron sputtering apparatus is suggested, operated at radio frequency. A pressure of $10^{-3}$ mbar is used. The silicon oxide is sputtered off high-purity quartz glass and deposited on the dental prosthesis part located in the vacuum chamber.

All apparatus heretofore proposed, and all the methods, are expensive, and equipment-intensive. The methods and apparatus all utilize evacuated chambers within which the dental prosthesis parts are coated.

THE INVENTION

It is an object to simplify the apparatus for applying an adhesion-promoting silicon oxide layer on a dental prosthesis, and a method for such application, which is simple, can be carried out under ordinary atmospheric conditions, and which is suitable for dental prosthesis part both of noble metals as well as of non-noble metals or their respective alloys.

Briefly, a source of silicon oxide is used which includes a flame hydrolysis burner in which, to the flame, a silicon oxide-generating gas or substance is added. At least one, and preferably and suitably a plurality of dental prostheses, which are to be coated, are located on a support. The burner, to which a metered amount of gaseous silicon oxide compounds is supplied, when in operation, has a flame cone of a length L of at least about 15 cm and up to about 20 cm, and is operated at a gas stream speed of up to about 1 meter per second. The flame hydrolysis burner is located with respect to the dental prosthesis by a spacing distance D of at most about 15 cm; another condition of operation is that the length L of the flame cone exceeds the spacing distance D by only up to about 25%. The dental prosthesis and the flame hydrolysis burner are relatively moved, for example and preferably by mounting a plurality of dental prostheses on a turntable which, sequentially, pass by the flame hydrolysis burner.

A plurality of coatings can be applied, with intermediate cooling of the dental prosthesis, for example by locating the orifice of cooling fluid applied on the dental prosthesis in the direction of movement, downstream of the burner, of the prosthesis. The fluid supplied may be air or, preferably, a mixture of air and water, which is sprayed on the dental prosthesis after it has received a coating. The dental prosthesis dries as it is rotated, and, then, additional coatings can be applied thereon until the requisite thickness of the adhesion-promoting layer is obtained.

DRAWINGS

DETAILED DESCRIPTION

Figure 1:
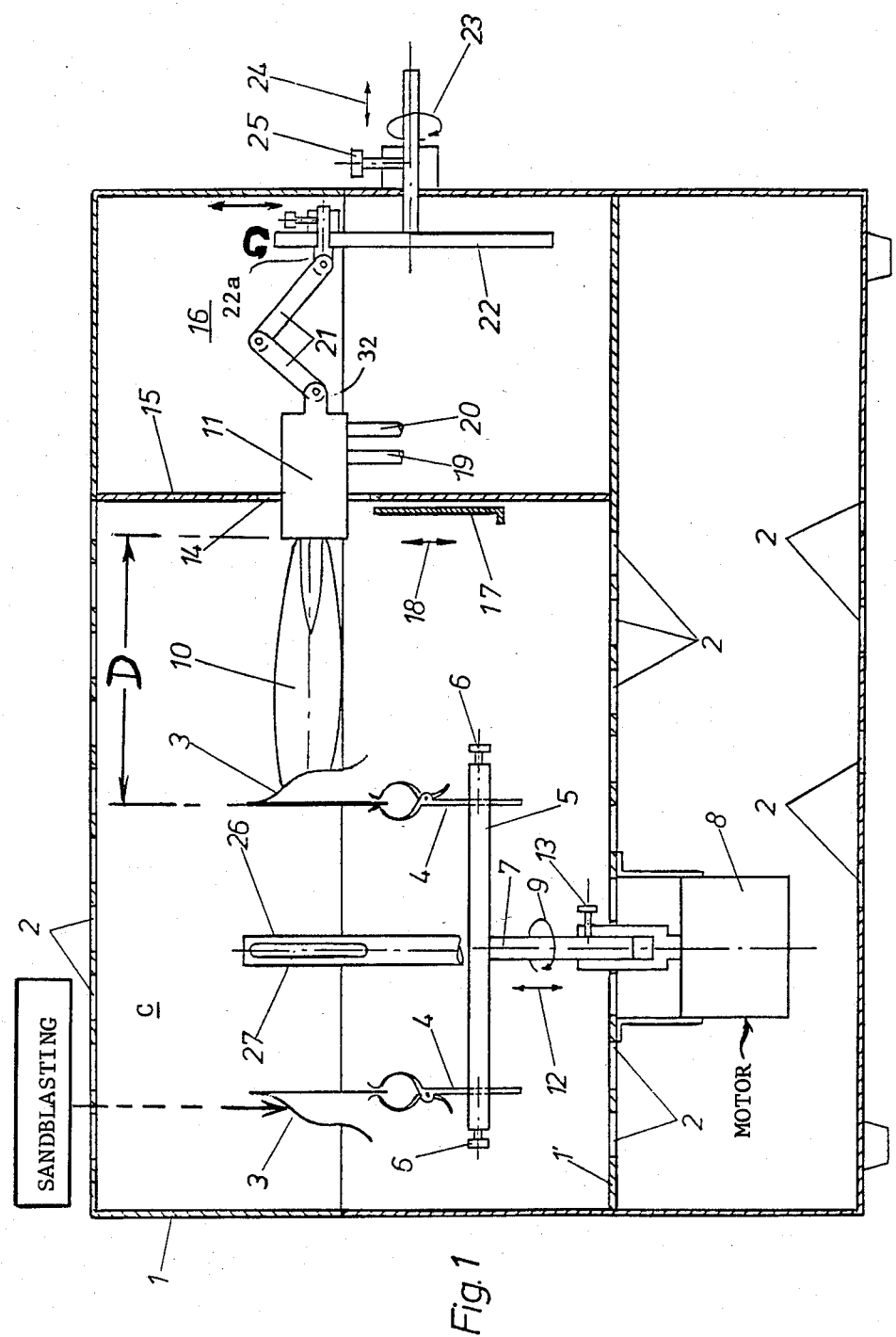
FIG. 1 illustrates, schematically and in part-vertical section, an apparatus to apply adhesion-promoting coatings on dental prosthesis parts.

A chamber C is provided having a bottom, a top, and an intermediate wall 1'. Both the top, the bottom, and the intermediate wall are provided with openings or apertures 2 to provide for ventilation within the chamber. Lateral doors may be fitted in the chamber, and both the top as well as the bottom may be made removable or pivotably secured to provide ready access to the inside of the chamber. Hinges and the like have been omitted from the drawing for clarity, and can be applied in any suitable and desired manner.

Dental prosthesis parts 3 are located within the chamber C. The dental prostheses 3 are secured to holders, for example clamps 4, which are fitted in a holding spider or wheel 5 and secured in the spider or wheel 5 by clamping screws 6. The holders 4 may also be made of flexible material in order to improve fine adjustment of positioning of the dental prosthesis parts—which are not necessarily always identical—with respect to a flame hydrolysis burner 11. The spider or wheel, in short a turntable, 5 is held by a shaft 7, coupled to a motor 8, and rotated as schematically indicated by the arrow 9. The turntable 5, as schematically indicated by the double arrow 12, is vertically adjustably positioned on shaft 7 in order to properly locate the respective dental prosthesis parts 3 in optimal position with respect to the flame or flame cone 10 emanating from the flame hydrolysis burner 11. A clamping screw 13 positions the shaft in a selected vertical level.

The axis of rotation of the shaft 7 could also be located essentially parallel to the flame hydrolysis burner.

The flame hydrolysis burner, as best seen in FIG. 1, is separated from the region of the chamber within the housing 1 by a separating wall 15 formed with an opening 14. The flame hydrolysis burner can be retracted into the burner chamber 16 within the structure 1 when the apparatus is out of operation. In that case, preferably, a cover plate 17 is applied over the opening 14, moved, as desired, in accordance with the direction of the double arrow 18, by being upwardly and downwardly slidable.

The flame hydrolysis burner 11 is supplied with air over a supply connection 19, and further is supplied with combustion gas over a supply connection 20. A suitable and preferred combustion gas is propane. A silicon compound is supplied, in gaseous form, in which, preferably, an oxidizable gaseous silicon compound is added to the air supply.

The flame hydrolysis burner 11 is linked by a settable connecting link 21, which can be clamped in position by suitable clamping screws, not specifically shown, to a holder 22. Holder 22, as indicated by arrow 23, can be rotated by hand and, as illustrated by arrow 24, can be moved back-and-forth. The optimum operating position is then fixed by tightening a set screw 25.

OPERATION

An optimum operating condition is so selected that, in the apparatus shown, the flame cone 10 is essentially horizontal. The maximum distance between the forward edge of the burner and the most remote part of the prosthesis 3 should be, at the most, about 15 cm. This distance is shown in FIG. 1 as D. The length L of the flame cone 10—dimension shown only in FIG. 2 for clarity—is, at least, about 15 cm, and at the most 20 cm.

A cooling device 26 is located within chamber 1, offset by 90° with respect to the direction of the flame cone 10.

METHOD OF COATING DENTAL PROSTHESIS PARTS OR FRAMES 3

The closing shield 17 is lowered to the position shown in FIG. 1, and the flame hydrolysis burner is passed through the opening 14 and placed in position. The position of the flame hydrolysis burner is so adjusted that the flame cone will be directed towards oppositely positioned dental prosthesis parts 3, by level positioning the axis of rotation of the shaft 7 of the turntable 5 and/or by height positioning and/or rotation of the holders 4 within the reception openings therefor in the turntable 5; and/or by rotation and back-and-forth adjustment of clamp 22a and holder 22, in accordance with arrows 23, 24. After optimizing the position of the burner 14 with respect to all of the dental prostheses parts 3 located on the turntable 5, motor 8 is started and the turntable is slowly rotated, for example at a speed of about 30 rpm. Air and fuel are then supplied to the connections 19, 20, respectivley, and oxidizable silicon compounds to the flame hydrolysis burner are opened, and the flame hydrolysis burner is ignited.

The rotating dental prosthesis parts 3 are sequentially exposed to the flame cone 10 of the flame hydrolysis burner 11, and the silicon oxide-containing adhesion-promoting layer will precipitate or deposit on the dental prosthesis parts 3.

The speed of rotation of the turntable 5 is so adjusted or controlled that, during one rotation of the turntable 5, the coated dental prosthesis 3 will cool sufficiently until they are again exposed to the flame cone 10 for deposition of a further, thin silicon oxide-containing coating or layer.

Cooling can be enhanced by the cooling apparatus 26 which supplies cooling for the dental prostheses 3, by projecting cooling air or an air-water mixture on the prostheses. The cooling device 26 is, preferably, formed as a slit nozzle with a vertically extending nozzle slit 27.

After several revolutions, and when the dental prosthesis parts 3 have received a sufficiently thick coating of the silicon oxide adhesion-promoting layer, air and fuel supply as well as silicon supply to the burner is turned off, and the burner retracted into the burner chamber 16, for example by loosening set screws connecting the links 21. The closing shield 17 is then closed.

The dental prosthesis parts or frames 3 can then be removed from the coating chamber C, and may be further treated, for example as described in the referenced U.S. Pat. No. 4,364,731, that is, by coating with a commercial dental plastic material, using, for example, a silane-containing coating.

Preferably, and in advance of placing the prostheses in the holders 4, they are thoroughly cleaned and sandblasted as schematically shown by the box "sandblasting". This step, as such, is conventional.

Figure 2:
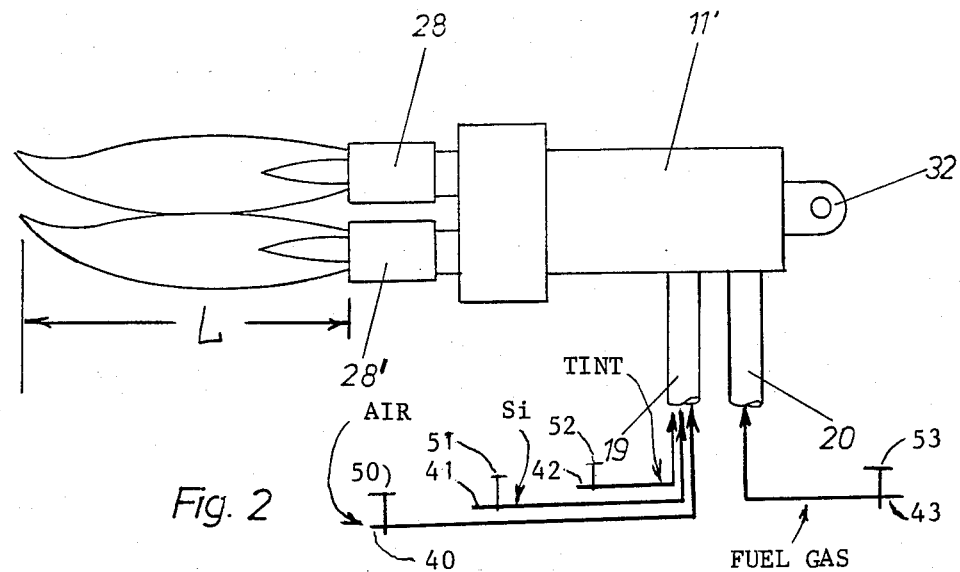
FIG. 2 is a schematic illustration of a double-orifice burner suitable for use in the apparatus of FIG. 1.
Figure 3:
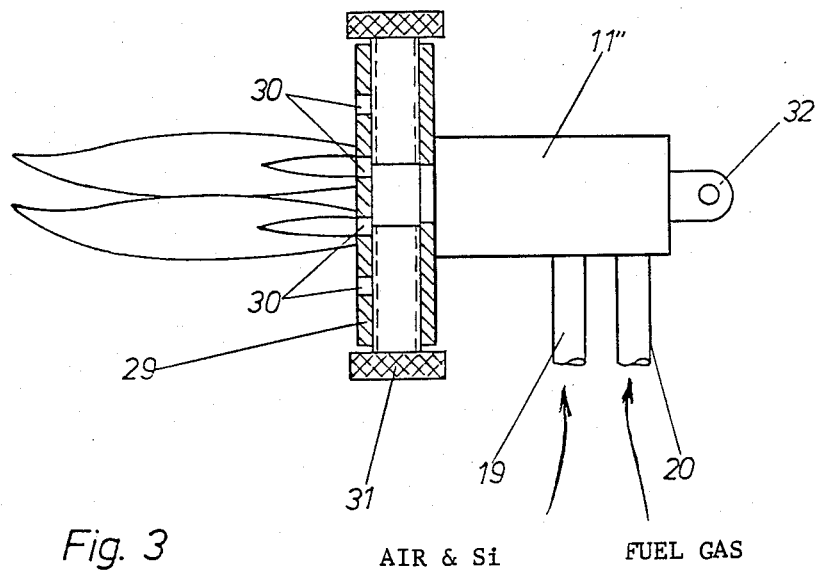
FIG. 3 is a side view, partly in section, of a flame hydrolysis burner with adjustable nozzle openings.

FIGS. 2 and 3 illustrate, in highly schematic form, other embodiments of flame hydrolysis burners which may be substituted for the burner 11 of FIG. 1, and which can be connected by attachment tabs 32 to the linkage 21.

The burner 11' of FIG. 2 differs from the burner 11 of FIG. 1 in that a double burner is provided, having two burner heads 28, 28', located one above each other. It is, of course, equally possible to locate the burners adjacent each other.

FIG. 3 illustrates a flame hydrolysis burner 11" which differs from the burner 11 of FIG. 1 in providing a single burner opening 29 which leads to a manifold having a plurality of exit openings 30. The number or pass-through diameter of the exit openings 30 can be changed, for example by sliding or rotating an aperture control member 31 within the manifold 29.

The apparatus has the advantage that it is readily possible to move the dental prosthesis part or the base frame, made of metal, during the coating with respect to the cone of the flame of the flame hydrolysis burner so that, sequentially, different surface portions of the prosthesis can be exposed to the flame cone.

Locating all the prosthesis elements on a turntable has the advantage that the dental prosthesis parts 3, during a rotation of the turntable, can cool sufficiently before a further silicon oxide-containing adhesion-promoting layer is being applied. The cooling device 26 preferably is located at an angular offset of from between 20° to 120°, preferably about 90°, with respect to the flame hydrolysis burner 11. It may be located, and preferably is located, next to the turntable.

The turntable is relatively movable upwardly and downwardly with respect to the flame cone 10 of the flame hydrolysis burner to insure optimum adjustment of the position of the dental prosthesis with respect to the coating effect obtained by the flame cone. Optimal adjustment is further obtained by locating the burner 11 in accordance with the adjustment provided, as schematically shown by arrows 23, 24. The linkage 21 may be provided with preset adjustment markers so that an adjustment by the linkage 21 which is once made is reproducible. Linkage 21 is used to withdraw the burner 11 into the chamber 16. By setting the various adjustments—clamping screw 13, clamp 22a, set screw 25 and the clamping screw 6—optimum placement of the respective prosthesis elements 3 with respect to the burner cone 10 is insured.

Various other arrangements of adjusting the burner, so that the flame cone 10 will have the appropriate characteristic with respect to the prostheses 3, may be used.

Fine adjustment of the burner flame can be easily obtained by changing the size and throughput of flame gases, as well as the size of the burner itself—see FIG. 3. If the burner has a slit-type nozzle, a controller plate, for example a knife edge, partially obstructing the slit nozzle, can be used. Burners having nozzle openings of circular cross section can be adjusted, as is well known, by placing a positioning needle or positioning cone more, or less, within the circular nozzle opening.

The flame hydrolysis burner is preferably operated with a combustion gas-air mixture. A preferred combustion gas or fuel gas is propane gas. An inorganic compound such as $SiH_4$ may be used as the oxidizing silicon compound; organic silicon compounds, likewise, may be used such as organosilane, organooxylsilane, organosiloxane, or a mixture of respective inorganic and organic, or only organic silicon compounds. If the oxidizable silicon compound is not available in gaseous form, it may be applied to the flame hydrolysis burner in vaporized form. In a preferred arrangement, the oxidizable silicon compound is supplied in gaseous form to the flame hydrolysis burner over the same connecting stub as the air being supplied for the fuel gas-air mixture, mixed in the burner in accordance with well known arrangements.

To obtain reproducible coating, and to be able to adjust the flame cone of the flame hydrolysis burner properly for optimum coating, the flame is preferably colored by addition of a coloring substance, for example volatile sodium or boron compounds. The coloring or tinting element is preferably supplied over the same supply stub as the oxidizable silicon compound, with metered supply of air, silicon compound, and tinting or coloring material. Metered supply is shown only in FIG. 2, in which, in the respective lines 40 supplying air, 41 supplying silicon compound, and 42 supplying tinting substance, valves 50, 51, 52 are located. A similar illustration has been omitted from the other drawings for simplicity.

Overall, the arrangement has the substantial advantage that it can be operated under normal, atmospheric conditions, that is, in ambient atmosphere, without vacuum or the like. In a preferred structure, the dental prostheses and their holder are located within the chamber C which is ventilated by ventilation slits 2, which permit circulation of ambient air through the chamber C. In this arrangement, the flame hydrolysis burner can be positioned in the same chamber as the articles to be coated. The additional chamber 16 is, however, preferred since additional protection against possible danger of fire is afforded, particularly if the linkage 21 is so arranged that it can be rapidly retracted from a preset position, with an externally accessible closure of the shield 17, thus shutting off the generation of flame from the burner, even if a control valve 53 in the fuel line 43 to stub 20 should not be immediately operable.

The arrangement permits deposition of intermediate layers, particularly suitable for enhancing adhesion of plastic on a metal substrate which includes silicon dioxide. Use of such an intermediate adhesion-promoting layer is described in the referenced U.S. Pat. No. 4,364,731. The arrangement also permits deposition of carbon-containing $SiO_x$ layers on dental prostheses. The carbon is then present, preferably, in form of remanent hydrocarbons, joined to the silicon. Adhesion-promoting layers with hydrocarbons have the particular advantage with respect to mere silicon dioxide layers that they have even better adhesion-promoting qualities between the dental plastic and the metal alloys used for prostheses. Further, they are more durable with respect to resistance to formation of fissures within the environment of a user's mouth, that is, under influence of moisture, changes in temperatures, and mechanical stresses applied thereto. Optimal results can be obtained with deposited silicon oxide-containing adhesion-promoting layers, having a carbon content of between 5% to 40% (by weight) of the adhesion-promoting layer. Obtaining such layers with the carbon content, in accordance with the present invention, is achieved by carrying the prosthesis part 3 to the forward third portion of the flame cone of the flame hydrolysis burner, and operating the flame hydrolysis burner with a carbon-containing fuel gas-air mixture, to which the above-referenced oxidizable silicon compound is admixed in metered or dosed amounts. To promote the best possible adhesion, it is preferred to expose the dental prosthesis parts 3 to sandblasting in advance of application of the adhesion-promoting layer. For sandblasting, corundum, with an average particle size of 0.25 mm, or more, has been found suitable.

We claim:

1. Apparatus, for applying a carbon-containing and silicon oxide-containing adhesion-promoting layer on a metallic dental prosthesis part (3), having
    a holder (4) supporting said prosthesis part (3) and a source (41) of silicon oxide,
    wherein, in accordance with the invention,
    the source of silicon oxide and carbon comprises at least one flame hydrolysis burner (11);
    means (41) are provided for supplying metered amounts of carbon-containing fuel gas and a silicon compound in vapor or gas form to said burner (11),
    said burner, in operation, having a flame cone of a length (L) of at least about 15 cm and up to about 20 cm, and having a gas stream speed of up to about 1 m/sec,
    said flame hydrolysis burner (11) being located with respect to the dental prosthesis part (3) by a spacing distance (D) of at the most about 15 cm while said layer is being applied,
    and said flame hydrolysis burner having supplied thereto metered amounts of carbon-containing fuel and air, controlled to provide a flame cone which has a length (L) which exceeds said spacing distance (D) by only up to about 25%, said silicon oxide in gaseous or vapor form being admixed with the air and fuel in the burner;
    and means (5, 8, 9) for relatively moving the dental prosthesis part (3) and said flame hydrolysis burner (11) in a direction to pass the dental prosthesis part (3) in front of said burner and hence through said flame cone.

2. Apparatus according to claim 1, wherein said relative moving means includes means (5) for moving the holder (4) supporting the dental prosthesis part relative to the flame hydrolysis burner.

3. Apparatus according to claim 1, wherein the relative moving means (5, 8, 9) comprises a turntable (5);
    and a plurality of holders (4) for a plurality of dental prosthesis parts (3), secured to said turntable, are provided.

4. Apparatus according to claim 3, wherein the level of said turntable (5) is height-adjsutable (12) with respect to the flame hydrolysis burner (11).

5. Apparatus according to claim 1, further including means (22a) for height-adjusting the burner (11) with respect to the dental prosthesis part (3) supported in the holder (4).

6. Apparatus according to claim 1, further including a rotatable support (22) connected to and rotatably supporting the burner (11).

7. Apparatus according to claim 6, including an adjustable holding link (21) connecting and supporting the burner (11) on said rotatable support (22).

8. Apparatus according to claim 1, wherein the burner is oriented to project the flame cone (10) in an essentially horizontal direction.

9. Apparatus according to claim 1, wherein the flame hydrolysis burner (11) comprises a nozzle opening (30) of variable size.

10. Apparatus according to claim 1, further including a cooling apparatus located at an angle between about 20° to 120° with respect to the orientation of the flame cone (10).

11. Apparatus according to claim 1, further including a housing (1) defining a ventilated chamber (C), the holder (4) and the dental prostheses (3) supported thereby being located within said chamber.

12. Apparatus according to claim 11, wherein the flame hydrolysis burner (11) is located in the chamber (C).

13. Apparatus according to claim 11, further including a separating wall (15) separating the chamber (C) into two chamber portions including a burner chamber (16), said separating wall being formed with a closeable opening (14, 17);

and wherein the flame hydrolysis burner is located in the burner chamber, and movable from a position wholly within the burner chamber to a position projecting through said opening.

14. Apparatus according to claim 1, wherein the flame hydrolysis burner comprises two burner heads (28) located parallel to each other.

15. Apparatus according to claim 1, further including means (42) for supplying a tinting compound to the fuel-gas mixture being supplied to the burner for coloring the flame of the burner.

16. Apparatus according to claim 1, wherein said holder (4) supporting the dental prosthesis (3) is bendable or flexible.

17. A process for applying a carbon-containing and silicon oxide-containing adhesion-promoting layer to a metallic dental prosthesis part (3), in an apparatus having a holder (4) supporting said prosthesis part (3);
at least one flame hydrolysis burner (11); and
means (5, 8, 9) for relatively moving the dental prosthesis part (3) and said flame hydrolysis burner (11); comprising the steps of (a) supplying ignition energy and controlled amounts of carbon-containing fuel gas and air to said hydrolysis burner;

(b) controlling said burner (11) to provide a flame cone which has a length (L) of at least about 15 cm and up to about 20 cm, and having a gas stream speed of up to about 1 m/sec;

(c) supplying a metered amount of a silicon compound in vapor or gas form to said burner (11);

(d) relatively moving said flame hydrolysis burner (11) and the metallic dental prosthesis part (3) at least once to with a distance (D) of each other of, at the most, about 15 cm, so that said part (3) passes within said flame cone, thereby depositing on said metallic part (3) a layer of silicon oxide which includes 5% to 40%, by weight, of carbon; and (e) removing said prosthesis part (3) from said flame cone until said deposited layer cools and solidifies.

18. A process according to claim 17, wherein said step of applying the silicon oxide layer comprises passing the dental prosthesis part (3) through the forward third of a flame cone of a flame hydrolysis burner (11); and including the step of supplying to said burner a fuel gas which includes carbon, air, and an oxidizable silicon compound in gaseous or vapor form.

19. A process according to claim 18, further including the step of sandblasting the dental prosthesis part (3) before subjecting said dental prosthesis part to the forward third of the flame cone of the flame hydrolysis burner (11).

20. The coated metallic dental prosthesis product (3) made by the process of claim 17.

* * * * *

UNITED STATES PATENT AND TRADEMARK OFFICE
CERTIFICATE OF CORRECTION

PATENT NO. : 4,600,390

DATED : July 15, 1986

INVENTOR(S) : Roland GOBEL et al

It is certified that error appears in the above-identified patent and that said Letters Patent is hereby corrected as shown below:

Claim 1, column 6, line 43 change "oxide" to -- compound --

Signed and Sealed this

Eighth Day of November, 1988

Attest:

DONALD J. QUIGG

Attesting Officer

Commissioner of Patents and Trademarks